(12) United States Patent
Bosley, Jr. et al.

(10) Patent No.: US 8,541,032 B2
(45) Date of Patent: Sep. 24, 2013

(54) TISSUE GRAFT COMPOSITION

(71) Applicant: Miles Grody, Columbia, MD (US)

(72) Inventors: Rodney W. Bosley, Jr., Chester Springs, PA (US); Clay Fette, Severna Park, MD (US)

(73) Assignee: ACell, Inc., Columbia, MD (US)

( * ) Notice: Subject to any disclaimer, the term of this patent is extended or adjusted under 35 U.S.C. 154(b) by 0 days.

(21) Appl. No.: 13/649,522

(22) Filed: Oct. 11, 2012

(65) Prior Publication Data
US 2013/0035768 A1 Feb. 7, 2013

Related U.S. Application Data

(62) Division of application No. 12/507,338, filed on Jul. 22, 2009, now Pat. No. 8,298,586.

(51) Int. Cl.
*A61K 35/12* (2006.01)
*A61K 35/32* (2006.01)

(52) U.S. Cl.
USPC ............ 424/572; 424/574; 424/443; 424/444

(58) Field of Classification Search
None
See application file for complete search history.

(56) References Cited

U.S. PATENT DOCUMENTS

| | | | |
|---|---|---|---|
| 3,562,820 A | 2/1971 | Braun | |
| 4,439,521 A | 3/1984 | Archer et al. | |
| 4,703,108 A | 10/1987 | Silver et al. | |
| 4,776,853 A | 10/1988 | Klement et al. | |
| 4,780,450 A | 10/1988 | Sauk et al. | |
| 4,801,299 A | 1/1989 | Brendel et al. | |
| 4,829,000 A | 5/1989 | Kleinman et al. | |
| 4,902,508 A | 2/1990 | Badylak et al. | |
| 4,956,178 A | 9/1990 | Badylak et al. | |
| 5,275,826 A | 1/1994 | Badylak et al. | |
| 5,281,422 A | 1/1994 | Badylak et al. | |
| 5,336,616 A | 8/1994 | Livesey et al. | |
| 5,352,463 A | 10/1994 | Badylak et al. | |
| 5,372,821 A | 12/1994 | Badylak et al. | |
| 5,445,833 A | 8/1995 | Badylak et al. | |
| 5,516,533 A | 5/1996 | Badylak et al. | |
| 5,554,389 A * | 9/1996 | Badylak et al. | 424/558 |
| 5,573,784 A | 11/1996 | Badylak et al. | |
| 5,607,590 A | 3/1997 | Shimizu | |
| 5,618,312 A | 4/1997 | Yui et al. | |
| 5,641,518 A | 6/1997 | Badylak et al. | |
| 5,695,998 A | 12/1997 | Badylak et al. | |

(Continued)

FOREIGN PATENT DOCUMENTS

| | | |
|---|---|---|
| DE | 19828726 | 1/1999 |
| EP | 0772033 A1 | 5/1997 |

(Continued)

OTHER PUBLICATIONS

International Search Report and Written Opinion of the ISA issued in a concurrently filed PCT application PCT/US2010/042698, mailed on Mar. 7, 2011; 9 pages.*

Badylak et al., "Small intestinal submucosa: a substrate for in vitro cell growth," J. Biomat. Science 9:863-88 (1988).*

Badylak et al., "Endothelial cell adherence to small intestinal submucosa: an acellular bioscaffold," Biomaterials 20:2257-2263 (1999).*

(Continued)

*Primary Examiner* — Allison Ford
(74) *Attorney, Agent, or Firm* — Burns & Levinson, LLP

(57) ABSTRACT

Disclosed are tissue graft compositions made of materials having different densities, methods of making, and methods of treatment for restoring tissues in a patient.

18 Claims, 8 Drawing Sheets

(56) References Cited

U.S. PATENT DOCUMENTS

| | | |
|---|---|---|
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,866,414 A | 2/1999 | Badylak et al. |
| 5,866,415 A | 2/1999 | Villeneuve et al. |
| 5,869,041 A | 2/1999 | Vandenburgh |
| 5,885,619 A | 3/1999 | Patel et al. |
| 5,899,936 A | 5/1999 | Goldstein |
| 5,916,266 A | 6/1999 | Yui et al. |
| 5,997,575 A | 12/1999 | Whitson et al. |
| 6,051,750 A | 4/2000 | Bell |
| 6,087,157 A | 7/2000 | Badylak et al. |
| 6,096,347 A | 8/2000 | Geddes et al. |
| 6,126,686 A | 10/2000 | Badylak et al. |
| 6,171,344 B1 | 1/2001 | Atala |
| 6,206,931 B1 | 3/2001 | Cook et al. |
| 6,322,593 B1 | 11/2001 | Pathak et al. |
| 6,376,244 B1 | 4/2002 | Atala |
| 6,432,712 B1 | 8/2002 | Wolfinbarger, Jr. |
| 6,454,804 B1 | 9/2002 | Ferree |
| 6,455,311 B1 | 9/2002 | Vacanti |
| 6,479,064 B1 | 11/2002 | Atala |
| 6,485,723 B1 | 11/2002 | Badylak et al. |
| 6,485,969 B1 | 11/2002 | Asem et al. |
| 6,572,650 B1 | 6/2003 | Abraham et al. |
| 6,576,265 B1 | 6/2003 | Spievack |
| 6,579,538 B1 | 6/2003 | Spievack |
| 6,613,348 B1 | 9/2003 | Jain |
| 6,783,776 B2 | 8/2004 | Spievack |
| 6,827,966 B2 | 12/2004 | Qiu et al. |
| 6,849,273 B2 | 2/2005 | Spievack |
| 6,852,339 B2 | 2/2005 | Spievack |
| 6,861,074 B2 | 3/2005 | Spievack |
| 6,869,619 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 7,160,333 B2 | 1/2007 | Plouhar et al. |
| 2002/0115208 A1 | 8/2002 | Mitchell et al. |
| 2002/0131933 A1 | 9/2002 | Delmotte |
| 2002/0172705 A1 | 11/2002 | Murphy et al. |
| 2003/0039742 A1 | 2/2003 | Qiu et al. |
| 2003/0054022 A1 | 3/2003 | Spievack |
| 2003/0059404 A1 | 3/2003 | Spievack |
| 2003/0059405 A1 | 3/2003 | Spievack |
| 2003/0059406 A1 | 3/2003 | Spievack |
| 2003/0059407 A1 | 3/2003 | Spievack |
| 2003/0059409 A1 | 3/2003 | Spievack |
| 2003/0059410 A1 | 3/2003 | Spievack |
| 2003/0059411 A1 | 3/2003 | Spievack |
| 2003/0064111 A1 | 4/2003 | Spievack |
| 2003/0064112 A1 | 4/2003 | Spievack |
| 2003/0133916 A1 | 7/2003 | Spievack |
| 2003/0133967 A1 | 7/2003 | Ruszczak |
| 2003/0211130 A1 | 11/2003 | Sanders et al. |
| 2004/0043006 A1 | 3/2004 | Badylak et al. |
| 2004/0175366 A1 | 9/2004 | Badylak |
| 2005/0106207 A1 | 5/2005 | Qiu et al. |
| 2005/0175659 A1 | 8/2005 | Macomber et al. |
| 2005/0249772 A1 | 11/2005 | Malaviya et al. |
| 2005/0283256 A1 | 12/2005 | Sommerich et al. |
| 2007/0254041 A1 | 11/2007 | Drapeau et al. |
| 2007/0254042 A1 | 11/2007 | Drapeau et al. |
| 2011/0020420 A1 | 1/2011 | Bosley |

FOREIGN PATENT DOCUMENTS

| | | |
|---|---|---|
| WO | 9300441 | 1/1993 |
| WO | 9524873 | 9/1995 |
| WO | 9717038 | 5/1997 |
| WO | 9737613 | 10/1997 |
| WO | 9822158 | 5/1998 |
| WO | 9325546 | 6/1998 |
| WO | 9825545 | 6/1998 |
| WO | 9825637 | 6/1998 |
| WO | 9846165 | 10/1998 |
| WO | 9919005 | 4/1999 |
| WO | 0015765 | 3/2000 |
| WO | 0214480 | 2/2002 |
| WO | 03043674 | 5/2003 |
| WO | 2005094694 | 10/2005 |

OTHER PUBLICATIONS

Badylak et al., "Marrow-derived cells populate scaffolds composed of xenogeneic extracellular matrix," Experimental Hematology 29:1310-1318 (2001).*.

Badylak et al., "Resorable Bioscaffold for Esophageal Repair in a Dog Model," Journal of Pediatric Surgery 35:7:1097-1103 (2000).*.

Dahms et al., "Bladder Acellular Matrix Graft in Rats: Its Neurophysiologic Properties and mRNA Expression of Growth Factors TGF-α and TGF-b," Neurology and Urodynamics 17:37-54 (1998).*.

Dahms et al., "Composition and biomechanical properties of the bladder acellular matrix graft: comparative analysis in rat, pig and human," British Journal of Urology 8:411-419 (1998.).*.

Dahms et al., "Free Ureteral Replacement in Rats: Regeneration of Ureteral Wall Components in the Acellular Matrix Graft," Urology 50(5) 818-825 (1997).*.

Hadlock et al., "A New Artificial Nerve Graft Containing Rolled Schwann Cell Monolayers," Microsurgery 21:96-101 (2001).*.

Lakey et al., "Improved Islet Survival and In Vitro Function Using Small Intestinal Submucosa," Transplantation Proceedings 30:383 (1998).*.

Lindberg et al., "Porcine small intestinal submucosa (SIS): a bioscaffold supporting in vitro primary human epidermal cell differentiation and synthesis of basement membrane proteins," Burns 27:254-266 (2001).*.

Mouri et al., "Defenestration of the Sinusoidal Endothelial Cell in a Rat Model of Cirrhosis," Hepatology 17:5:891-897 (1993).*.

Pariente et al., "In Vitro Biocompatibility Assessment of Naturally Derived and Synthetic Biomaterials using Normal Human Urothelial Cells," J. Biomed. Mater. Res. 55-33-39 (2001).*.

Pariente et al., "In Vitro Biocompatibility Assessment of Naturally Derived and Synthetic Biomaterials using Normal Human Bladder Smooth Muscle Cells," The Journal of Urology 167:1867-1871 (2002).*.

Peel et al., "Formation of a SIS-cartilage composite graft in vitro and its use in the repair of articular cartilage defects," Tissue Eng. 4:143-155 (1998).*.

Piechota et al., "Bladder acellular matrix graft; in vivo functional properties of the regenerated rat bladder," Urol Res 27:206-213 (1999).*.

Piechota et al., "Functional rat bladder regeneration through xenotransplantation of the bladder acellular matrix graft," British Journal of Urology 81:548-559 (1998).*.

Piechota et al., "In Vitro Functional Properties of the Rat Bladder Regenerated by the Bladder Acellular Matrix Graft," Journal of Urology 159-1717-1724 (1998).*.

Probst et al., "Homologous bladder augmentation in dog with the bladder acellular matrix graft," BJU International 85:362-371 (2000).*.

Rosenthal et al., "The Mucosal Invasion Model," Arch Otolaryngol Head Neck Surgery 127:1467-1470 (2001).*.

Voytik-Harbin et al., "Small intestinal submucosa: A tissue-derived extracellular matrix that promotes tissue-specific growth and differentiation of cells in vitro," Tissue Eng. 4:157-174 (1998).*.

Voytik-Harvie et al., "Three-dimensional imaging of extracellular matrix and extracellular matrix-cell interactions," Methods Cell Biol. 63:583-597 (2001).*.

Yoo et al., "Bladder Augmentation using Allogenic Bladder Submucosa Seeded with Cells," Urology 51(2):221-225 (1998).*.

Zhang et al., "Coculture of Bladder Urothelial and Smooth Muscle Cells on Small Intestine Submucosa: Potential Applications for Tissue Engineering Technology," The Journal of Urology 164:928-935 (2004).*.

* cited by examiner

TISSUE GRAFT COMPOSITION

CROSS REFERENCE TO RELATED APPLICATION

This application is a divisional application claiming priority to and the benefit of co-pending U.S. patent application Ser. No. 12/507,338, filed on Jul. 22, 2009, the entire contents of which are incorporated herein by reference.

TECHNICAL FIELD OF THE INVENTION

The present invention is related to tissue graft compositions, their method of making, and their use for restoration of tissues in a patient.

BACKGROUND

Tissue graft compositions made of devitalized native tissues have been widely used to restore damaged or missing tissues in patients. Typically these compositions are made from the extracellular matrix of tissues, for example, the submucosa of the intestine (SIS), or urinary bladder (UBS), and the epithelial basement membrane of for example, the urinary bladder (UBM). SIS, UBS, and UBM are described in U.S. Pat. Nos. 6,576,265, 6,579,538, 5,573,784, 5,554,389, 4,956,178, and 4,902,508, each of which is incorporated in their entirety by reference herein. Collectively these compositions are termed extracellular matrices (ECMs). These compositions alone generally have sufficient strength to be useful for aiding the restoration of tissues and organs that are not subjected to large forces or pressures. ECMs are typically used to repair tissues or organs at anatomic sites in the body that are different from the tissue or organ from which the ECM was derived.

Tissue graft compositions are sometimes layered. The layers include various ECMs which may be hydrated, dehydrated or lyophilized. The layers are mechanically compressed, vacuum compressed or "glued" to join one layer to the other to form the composition. Layering, in some cases, adds strength to the composition.

Restoration of tissues for which ECMs are used include epithelial tissues. Epithelial tissues have an epithelium. Restoration of epithelial tissues requires restoration of the epithelium and the underlying connective tissues layers of the epithelial tissue. Restoration of the epithelium occurs rapidly when the epithelial basement membrane is present. On the other hand, restoration of the connective tissue layers of epithelial tissues is slower than restoration of the epithelium, prolonging complete restoration of the damaged epithelial tissue.

SUMMARY OF THE INVENTION

According to one aspect, the invention is a tissue graft composition. In one embodiment, the tissue graft composition includes a plurality of layers and has at least two layers. At least one layer is an ECM having a density that differs from at least one of the other layers of the tissue graft composition. Each of the layers has a first planar surface and a second planar surface. Each layer of the tissue graft composition at least partially overlaps an adjacent layer of the tissue graft compositions.

In one embodiment, at least one of the layers of the tissue graft composition includes all of or at least a portion of the epithelial basement membrane such as a sheet form of epithelial basement membrane. In a further embodiment, the epithelial basement membrane such as the sheet form is positioned on an external planar surface of the tissue graft composition. In yet another embodiment, at least one of the layers is aponeurosis such as a sheet form of aponeurosis. The aponeurosis may be positioned on an external planar surface of the tissue graft composition or as an intermediate layer between two other layers each of which forms one of an external planar surface of the tissue graft composition. In a further embodiment, each of the layers is an ECM, while in another embodiment, at least one layer is a sheet of epithelial basement membrane and at least another layer is a sheet of aponeurosis. In a further embodiment, one of the two layers each forming an external planar surface of the tissue graft composition is a sheet of epithelial basement membrane.

In another embodiment, one of the layers of the tissue graft composition has raised elements and a second one of the layers has depressions. The raised elements of one of the layers mates with the depressions of the second one of the layers to join the first and second layers together.

In yet another embodiment, the tissue graft composition has at least one layer with a density that differs from at least one other layer. The difference of the at least one layer is in the range of about 400% to 125% more dense than the other layer.

In yet another embodiment, the tissue graft composition has one layer that is an intermediate layer positioned between two outer layers. The intermediate layer includes a plurality of perforations that extend from one surface of the intermediate layer to the opposing surface of the intermediate layer thereby forming a lumen in the intermediate layer that is substantially perpendicular to a first and second planar surface of said intermediate layer. In a further embodiment, the raised elements of the outer layers of the tissue graft composition are aligned with perforations of an intermediate layer. The raised elements are located in the lumen of the perforations.

In a further embodiment, two outer layers of the tissue graft construct are more hydrated relative to the intermediate layer.

According to another aspect, the invention includes a method for manufacturing a tissue graft composition. The method includes the steps of providing a first layer of planar biological material having a first density, providing a second layer of planar material comprising a second density that is less than the density of the first layer of material, and joining the first layer to the second layer. According to one embodiment of the method, at least a portion of the first or second layers comprises aponeurosis, while in another embodiment, at least a portion of the first or second layers comprises the entire, or at least a portion of epithelial basement membrane, for example, in a sheet form.

According to another embodiment, the method further includes the steps of introducing a third layer of material, introducing perforations into the third layer of material, introducing the third layer of material between the first and second layers and compressing together the first layer and the second layer of material so that the first layer of material and the second layer of material extend into the perforations of the third layer of material to join the first layer to the second layer and the third layer.

According to another embodiment, the method includes introducing perforations into the first layer of material, introducing columns into the second layer of material, and compressing the first layer and the second layer of material together so that the columns of the second layer of material are introduced into the perforations of the first layer of material to join the first layer to the second layer of material. According to a further embodiment, a method includes introducing a third layer, perforating the third layer of material, positioning the third layer of material between the first and second layers of material, and introducing the columns in the second layer of material through the perforations in the third layer of material to join together the first layer, second layer, and third layer of material.

According to another embodiment, the method includes perforating the first and second layers. In a further embodiment, the method includes introducing raised members into the first layer of material, introducing depressed members complementary to the raised members into the second layer of material, compressing the first layer and the second layer of material together wherein the raised members of the first layer of material intercalates with the depressed members of the second layer of material to join the first layer to the second layer. According to a further embodiment, the raised members or the depressed members are introduced into the first or second layer of material by stretching the material over a template to introduce the raised member or depressed member into the first or second layer of material. In an alternative embodiment, the raised members or the depressed members are introduced into the first or second layer of material by compressing the first or second layer of material on a template to introduce the raised member or depressed member into the material.

In a further embodiment, the template includes a first planar surface and a second planar surface and the compressing includes compressing the first or second layer of material between the first and second planar surface of the template. In yet another embodiment, the first material and the second material are hydrated materials when the first and second materials are compressed together, while in another embodiment, the first and second materials are dehydrated or lyophilized after compressing the first material to the second material.

In yet another aspect, the invention includes a method for restoring tissue damage of a joint, skin, an abdominal body wall, a thoracic body wall, a tendon, a ligament, or a hernia. As used herein, "Restore", "restored," "restoring," and "restoration" mean that tissue function and structure is substantially returned to its original condition by the patient's endogenous tissue repair mechanisms in combination with the tissue graft composition.

The method includes providing a composition comprising a first layer and a second layer of extracellular matrix wherein the second layer has a density at least 125% of the density of the first layer; and applying the composition to said joint, skin, abdominal body wall, thoracic body wall, tendon, ligament, or hernia. In one embodiment, the first layer comprises aponeurosis, while in another embodiment, the first layer comprises epithelial basement membrane. In another embodiment, the first layer comprises a plurality of perforations with each perforation having a lumen. The second layer is imperforated and the lumen of the perforations of the first layer encloses a portion of the second layer whereby the perforated first layer is joined to the non-perforated second layer. In another embodiment, the composition further includes a third layer wherein the first layer is positioned between and joined to the third layer and second layer.

In yet another embodiment of the method, the composition is implanted in the abdominal wall of a patient and said epithelial basement membrane is positioned on the peritoneal surface of the abdominal wall, while in a further embodiment, the composition is implanted in a joint of a patient and the epithelial basement membrane is positioned on the synovial surface of the joint. In yet another embodiment, the composition is implanted in the wall of the urinary bladder of a patient and the epithelial basement membrane is positioned on the urothelial side of said bladder wall. In another embodiment, the composition according to the invention is a vascular patch or a vascular graft. When the vascular graft or vascular patch is implanted in the wall of a vessel or the wall of the heart, the basement membrane side of the patch or graft is positioned on the luminal, i.e., the endothelial side of the vessel or heart.

According to one embodiment of the method, at least one of the layers of the composition is bioresorbed within 30 days, while in another embodiment, one of the layers is bioresorbed within 120 days.

According to another aspect, the invention includes a method for restoring an epithelial tissue at an anatomic site of a patient. The method includes the steps of providing a composition comprising a combination of layers comprising UBM comprising epithelial basement membrane, and an ECM comprising a devitalized portion of site-specific ECM derived from the anatomic site from a mammal, wherein the epithelial basement membrane is located on a surface of the composition, and implanting the composition at the anatomic site of the patient wherein the epithelial basement membrane is located on the epithelial side of the anatomic site.

BRIEF DESCRIPTION OF THE FIGURES

The foregoing and other objects, features and advantages of the present invention disclosed herein, as well as the invention itself, will be more fully understood from the following description of preferred embodiments and claims, when read together with the accompanying drawings. The drawings are not necessarily to scale, emphasis instead generally being placed upon illustrating the principles of the invention.

DETAILED DESCRIPTION OF THE INVENTION

Figure 1:
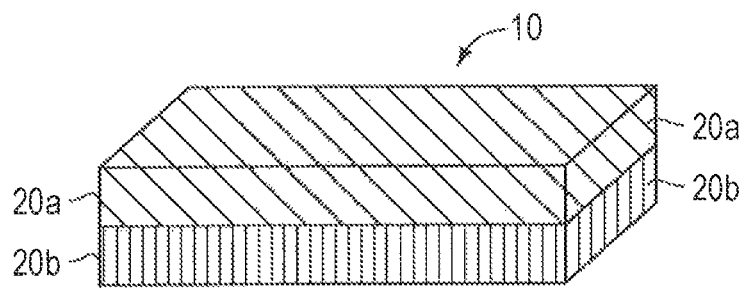
FIG. 1 illustrates a perspective view of an exemplary embodiment of the tissue graft composition according to the invention.

At anatomic sites in a body that are under prolonged or intermittent forces or pressures, the elasticity, rate of bioresorption, and strength of a tissue graft composition implanted at the site is important to tissue restoration. Where tissue restoration is slow at anatomic sites such as the abdominal wall, joints, or urinary bladder, for example, the tissue graft composition must be resistant to rupture or tearing and must persist at the implanted site sufficiently long to allow epithelial and connective tissue restoration to occur. The invention described herein addresses these challenges. The tissue graft composition of the invention has sufficient strength, elasticity, and durability to persist at the site of implantation for sufficient time to aid in restoration of the tissues being treated, at the same time the tissue graft composition is being replaced by the patient's own tissues.

In one aspect, the present invention is directed to a tissue graft composition that includes a plurality of layers, at least one of the layers having a density greater than at least one other layer and at least one of the layers being made from an extracellular matrix material (ECM). The term layer, as used herein, means generally a planar, sheet-like material that is rectangular, substantially rectangular, or elongated in shape. The ECM may be derived from native mammalian tissues including but not limited to submucosa, dermis, epithelial basement membrane, aponeurosis, fascia, tendon, ligament, smooth and skeletal muscle and treatment site-specific ECM. The native mammalian tissue source may be porcine, bovine, ovine, allogenic, or autogenic, for example. For example, the ECM may be SIS (small intestinal submucosa), UBS (urinary bladder submucosa or UBM (urinary bladder matrix) described in U.S. Pat. Nos. 6,576,265, 6,579,538, 5,573,784, 5,554,389, 4,956,178, and 4,902,508, each of which are incorporated by reference herein.

Briefly, SIS and UBS are made from gastrointestinal tissue and urinary bladder, respectively, by delaminating the submucosa from all other layers of the tissue source and retaining the submucosa to form a tissue graft composition. UBM is made by delaminating the epithelial basement membrane and, optionally, delaminating one or more of the deeper layers from the epithelial cells of the urinary bladder and retaining at least the epithelial basement membrane to form a tissue graft composition. Other tissues including, but not limited to, tissues of the gastrointestinal tract, e.g., esophagus, stomach, intestine, and skin may be used to make an ECM including epithelial basement membrane by delaminating the epithelial basement membrane from the epithelial cells and, optionally, one or more of the deeper layers of the tissue source.

One of the problems in applying prior art ECMs to anatomical sites that require a strong support composition, such as the abdominal wall or the soft tissues around joints such as the shoulder, knee, and hip joints, is that the known ECMs provide a readily bioresorbable scaffold that effects immediate, short-term repair, yet are not strong enough and are bioresorbed too rapidly to remain in position at the treatment site sufficiently long to achieve the objective of both endogenous epithelial tissue and connective tissue repair. Prior art ECMs, when applied to anatomical sites that are subjected to high pressures (e.g., body wall and joints) tend to fail because these ECMs do not have sufficient strength to withstand these forces and tear or rupture at the treatment site where the ECM is implanted before tissue restoration can take place.

In one embodiment of the present invention, the problem of fragility and rapid bioresorption of ECMs is addressed by a tissue graft composition in which one of the layers of ECM is devitalized native mammalian aponeurosis. The aponeurosis, because of its density, elasticity, and strength, in combination with other ECMs, for example, UBM, is useful for treatment of the abdominal wall, an anatomical site that is subjected to high intra-abdominal forces and pressures. Accordingly, the combination of the aponeurosis with, for example, UBM, provides significant advantages over SIS or UBS alone in repair of an abdominal hernia. The aponeurosis may also be combined with other ECMs for treatment of anatomic sites where aponeurosis is not found, for example, the rotator cuff tissues of the shoulder joint.

Prior to the present invention, one skilled in the art did not appreciate the advantages of aponeurosis. The aponeurosis is a particularly dense, sheet-like native connective tissue with significant unappreciated advantages over other ECMs, for example, submucosa. The aponeurosis is made primarily of native Type I collagen, is dense, elastic, and has exceptional strength and durability compared to other collagens that are found in the submucosa and epithelial basement membrane such as Type II, Type IV and Type VII collagen. The combination of aponeurosis with ECMs such as UBM and SIS provides a remarkably strong, dense, elastic backbone for scaffold ECMs that are typically not strong enough to withstand pressure, torque, and other forces such as tearing.

The aponeurosis, as well as other ECMs from treatment site specific organs, the urinary bladder wall, for example, are further advantageous compared to prior art ECMs because of their native elasticity which allows the implanted tissue graft composition when implanted at a tissue site to stretch and recoil much like the patient tissues at the treatment site, such as the abdominal wall and urinary bladder. The ability of the tissue graft composition of the invention to stretch and recoil in response to external forces minimizes the likelihood that the tissue graft composition will tear or rupture at the site of implantation.

The ECMs in the layers of the tissue graft composition of the invention may optionally retain native growth factors and other bioactive molecules. Among these are epidermal growth factor, TGF-alpha, TGF, beta, fibroblast growth factor, platelet derived growth factor, vascular endothelial growth factor, insulin-like growth factor, keratinocyte growth factor, and bone morphogenic protein to name a few. Growth factors may also be introduced into the ECM before implantation of the ECM.

In one embodiment according to the invention, the tissue graft composition of the invention has a plurality of layers, at least one of the layers having a different density than at least one of the other layers. As used throughout, density means mass per unit volume. The density of one layer may be in the range of about 400% to 125% of the density of another layer, preferably in the range of about 300% to 150%, more preferably 200% to 175%. The layers of the tissue graft composition are made from the same ECM, as described above, or, alternatively, different ECMs. The density of each layer may reflect the natural density of the ECM or may be a density introduced into the ECM by any of the means described below. For example, densities of the layers may range from 150 mg/cm$^3$ to 1800 mg/cm$^3$, more preferably from 150 mg/cm$^3$ to 1200 mg/cm$^3$, and most preferably from 150 mg/cm$^3$ to 600 mg/cm$^3$.

Tissue graft compositions according to the invention may be designed so that at least one layer of the composition has a density mimicking the strength of the native tissue it is used to replace while having at least a second less dense layer that is bioabsorbed more quickly than the dense layer, thereby allowing rapid cellular infiltration and vascularization of the tissue graft composition and release of bioactive factors as the less dense layer is quickly absorbed.

In the exemplary embodiment shown in FIG. 1, the tissue graft composition 10 of the invention has two layers, a first layer 20a being more dense than a second layer 20b. Each of the layers may have the same thickness or different thicknesses as long as one of the layers has a different density than the other layer, irrespective of the layers' thicknesses. The combination of layers is not limited to that depicted in FIG. 1. For example, there may be three, four, five, six or more layers with one or more layers having a different density than at least one of the other layers.

Figure 2:
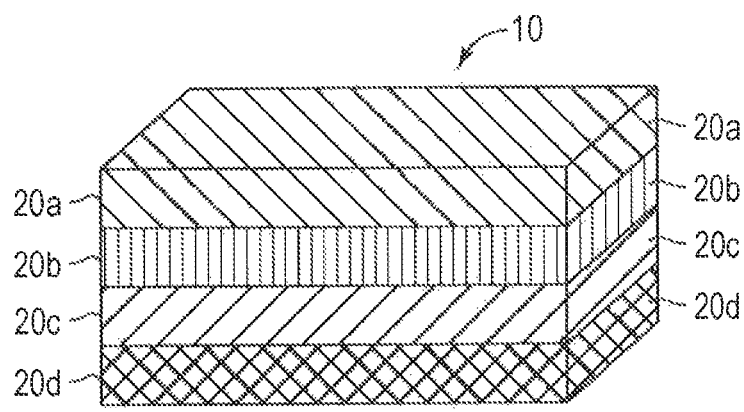
FIG. 2 illustrates a perspective view of an exemplary four layer embodiment of the tissue graft composition according to the invention.

Referring now to FIG. 2, in a particular embodiment of the invention, each of the layers 20a, 20b, 20c, and 20d of an exemplary four layer tissue graft composition 10 has a different density than each of the other layers.

Figure 3:
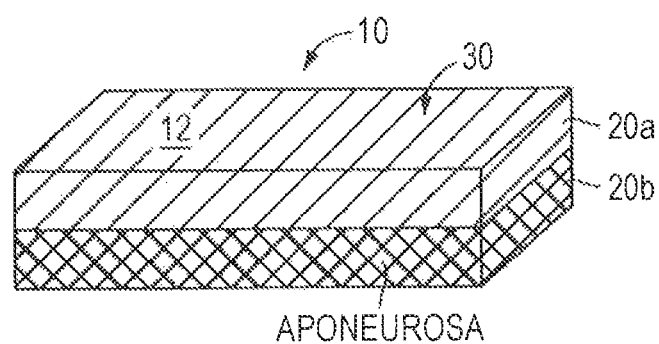
FIG. 3 illustrates a perspective view of an exemplary embodiment of the tissue graft composition according to the invention.

In one embodiment, the tissue graft composition of the invention has at least two layers, one of the layers made from aponeurosis and the other layer made from another ECM. Referring to FIG. 3, in a particular embodiment of this invention, one of the layers 20a is UBM and the other layer 20b is aponeurosis. In this embodiment the epithelial basement membrane 30 of UBM of layer 20a is located on an outer surface 12 of the tissue graft composition 10. One advantage of having the epithelial basement membrane on an outer surface of the tissue graft composition is preference by epithelial cells for the epithelial basement membrane for epithelial cell migration and attachment. Therefore, after implantation of the tissue graft composition at or near an anatomical site needing restoration in the patient, the availability of the epithelial basement membrane for the patient's own epithelial cell population may accelerate restoration of the patient's tissue by providing a preferred surface on which the patient's epithelial cells can readily migrate and attach.

In another aspect, the present invention is related to methods of making layers of ECM of different densities and methods for joining one layer to another layer of the tissue graft composition. Sheets of ECM can be dehydrated, hydrated, lyophilized, or mechanically or vacuum compressed to change their density. For example, in one embodiment of the tissue graft composition, one of the layers of ECM is hydrated to change its density while another layer of ECM is compressed, dehydrated, or lyophilized, but not hydrated.

Figure 4A:
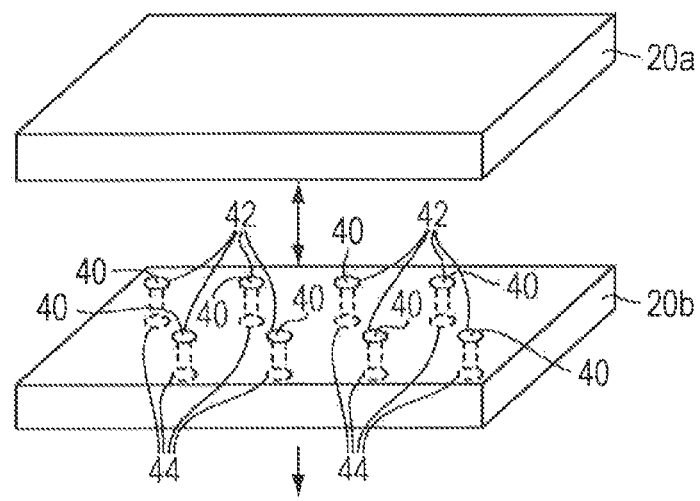
FIGS. 4A and 4B illustrate the steps in joining together two layers to form the tissue graft composition according to one embodiment of the invention.
Figure 4B:
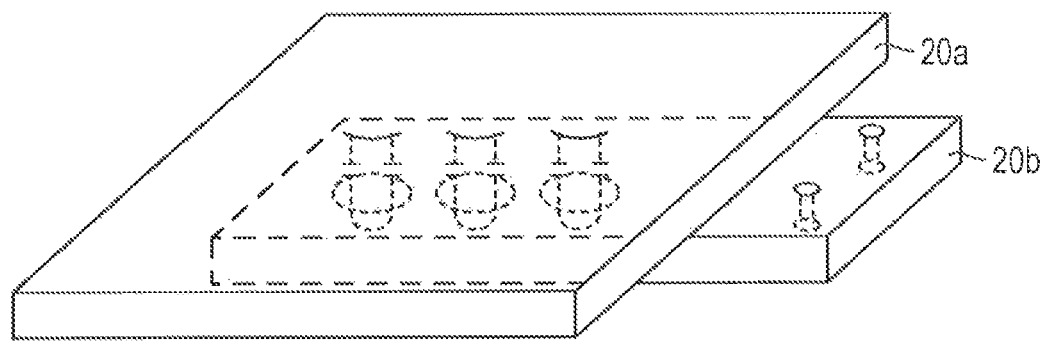

Various methods may be used to join one layer of ECM with another layer of ECM of a different density. Referring to FIGS. 4A-B, according to one embodiment of the method, a layer of non-perforated ECM 20a is provided. Another layer of perforated ECM 20b is provided which has at least two perforations 40 extending from one surface of the layer 20b to the other surface. A perforation may be made by a punch or drill or by chemical means. Each perforation 40 completely penetrates the layer 20b and has a lumen extending roughly perpendicular to the surface of the ECM from an opening 42 on one surface to an opening 44 on the other surface of the layer 20b. The diameter of the perforation is in the range of about 0.1 mm to 50 mm, preferably 0.5 mm to 20 mm, most preferably 5 mm to 10 mm. The perforations are spaced apart in the range of about 0.05 cm to 5 cm, preferably 0.25 cm to 3 cm, more preferably 0.5 cm to 2 cm. In one embodiment, the perforated layer is mechanically or vacuum compressed and the non-perforated layer is lyophilized. Alternatively, either layer may be hydrated, lyophilized or compressed.

In a particular embodiment, the non-perforated layer 20a is at least partially overlapped with the perforated layer 20b so that at least one of the perforations 40 of the perforated layer 20b is in contact with the surface of the non-perforated layer 20a. In one embodiment, the overlapped layers 20a, 20b are compressed together. By compressing together the layers, a portion of the non-perforated layer 20a is forced into the lumen of the perforations 40 in the perforated layer 20b that overlap the non-perforated layer 20a, illustrated in FIG. 4B. The resulting composition 10 with the perforated and non-perforated layers joined together, may be lyophilized, hydrated or dehydrated. Prior to implantation in a patient, the tissue graft composition may be re-hydrated.

According to another embodiment, a plurality of alternating non-perforated and perforated layers are compressed together as described above to obtain a tissue graft composition with layers of ECM that are joined together with at least one of the layers having a different density than at least one of the other layers.

Figure 5A:
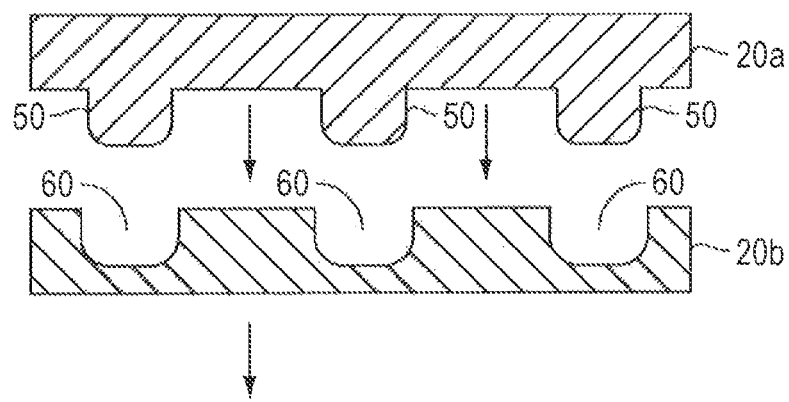
FIGS. 5A and 5B illustrate the steps in joining together two layers to form the tissue graft composition according to another embodiment of the invention.
Figure 5B:
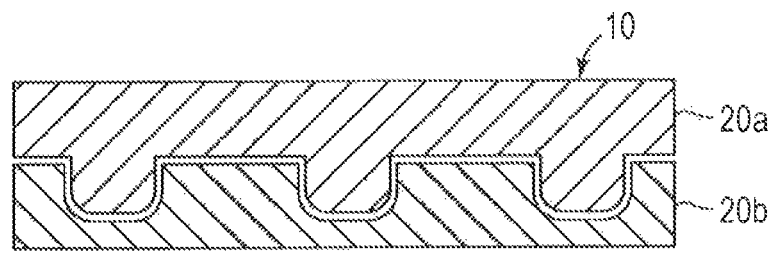

Referring to FIGS. 5A-B, in another embodiment of the method for making the invention, raised elements 50 such as a plurality of raised columns, pyramids, mounds, ridges or other elements that extend substantially perpendicular to the surface of the layer are introduced into a first layer 20a. A plurality of depressions 60, for example, dimples, cups, cylinders, valleys or perforations that extend substantially perpendicular to the surface into the body of the layer are introduced from the surface of the second layer 20b into the body of the second layer 20b. The plurality of depressions 60 in the second layer 20b corresponds in topographical distribution and size to the plurality of raised elements 50 in the first layer 20a. In one embodiment according to the invention, the raised elements 50 and the depressions 60 are introduced into the layer of ECM by compressing the ECM on a form or template (not shown) having the appropriate structural features on the face of the template for introducing the appropriate surface characteristic into or on the layer of ECM. Alternatively, the layer of ECM may be stretched over rather than compressed onto the face of the template.

Preferably, each layer is hydrated. The first layer 20a is at least partially overlapped with the second layer 20b so that at least one of the raised elements 50 aligns with and mates with at least one of the depressions 60 in the second layer 20b. The phrase "mates with" as used herein means that the tolerance between a raised element when introduced into a depression is small, i.e., the fit is tight enough to aid in irreversibly joining the layers together. In one embodiment, the first layer 20a and the second layer 20b are dehydrated, mated, and then hydrated.

Following overlap of the layers 20a and 20b, the layers 20a and 20b are compressed together. By compressing the layers together as shown in FIG. 5B, at least one of the raised elements 50 of the first layer 20a is introduced into at least one of the depressions 60 of the second layer 20b to join the first and second layers together. The resulting composition 10 with the first and second layers joined together, may undergo lyophilization, hydration, or dehydration. Prior to implantation in a patient, the tissue graft composition may be rehydrated.

According to another embodiment, a plurality of alternating layers are compressed together as described above to obtain a tissue graft composition with layers of ECM, at least one of which has a different density. For example, a first layer having a first density comprises depressions. A second layer having a density that is different than the first layer has raised elements that correspond to the depressions in the first layer. The second layer also has perpendicular elements. A third layer has depressions that correspond to the perpendicular elements in the second layer. The third layer also has perpendicular elements. A fourth layer has depressions that correspond to the perpendicular elements in the third layer and the fourth layer has perpendicular elements, and so on.

In another embodiment of making the invention, at least a first layer of ECM of a first density and a second layer of ECM of a second density are each separately hydrated and then compressed together to form a tissue graft composition.

Figure 6A:
FIGS. 6A-C illustrate the steps required to make a tissue graft composition of the invention wherein two sheets of ECM are layered one on top of the other and are perforated.
Figure 6B:
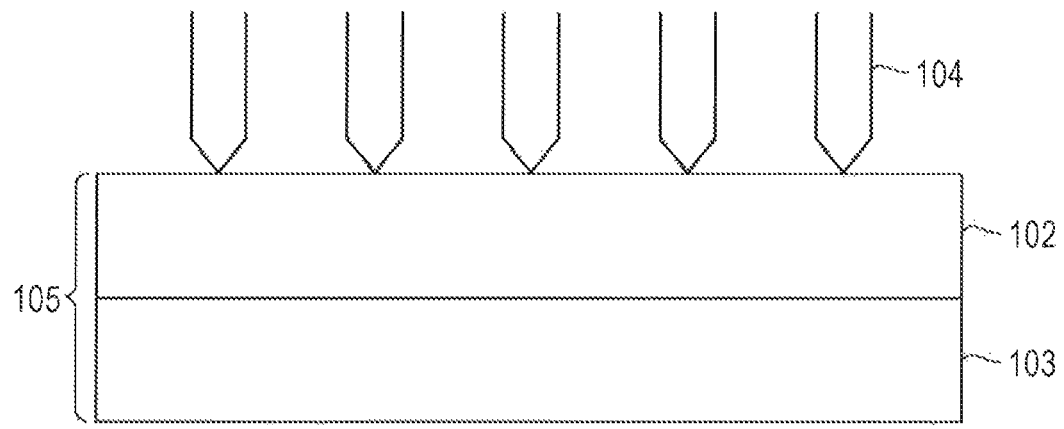
Figure 6C:
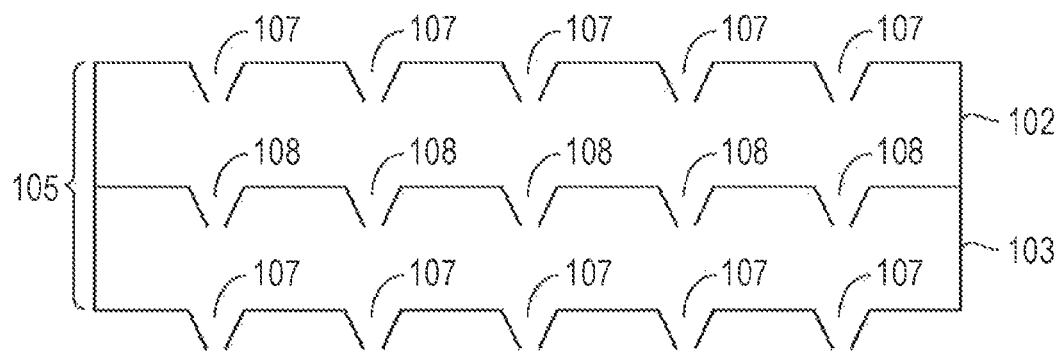

In another embodiment of the method of making the invention, as shown in FIG. 6A, at least a first layer 102 of a first density and a second layer 103 of a second density are each separately hydrated and then layered one on top of the other to form a tissue graft construct 105. As shown in FIGS. 6B-C, the construct 105 is then perforated by perforating members 104 to create a plurality of holes 107 in the surface of the first and second layers 102, 103. This permits portions of one layer of the construct to be pushed through the adjacent layer of the construct, resulting in a plurality of localized areas of bonding 108 between the first and second layers of the construct 102, 103.

Figure 7A:
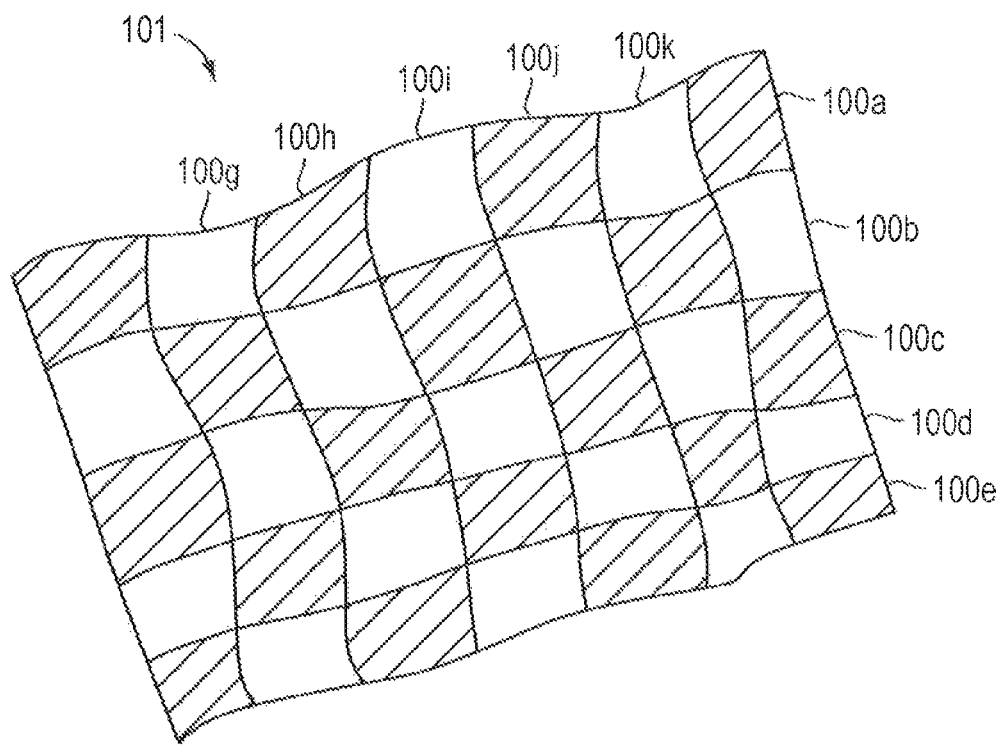
FIGS. 7A and 7B illustrate exemplary embodiments of the tissue graft composition which are sheets of ECM made from strips of ECM woven in a lattice-like fashion.
Figure 7B:
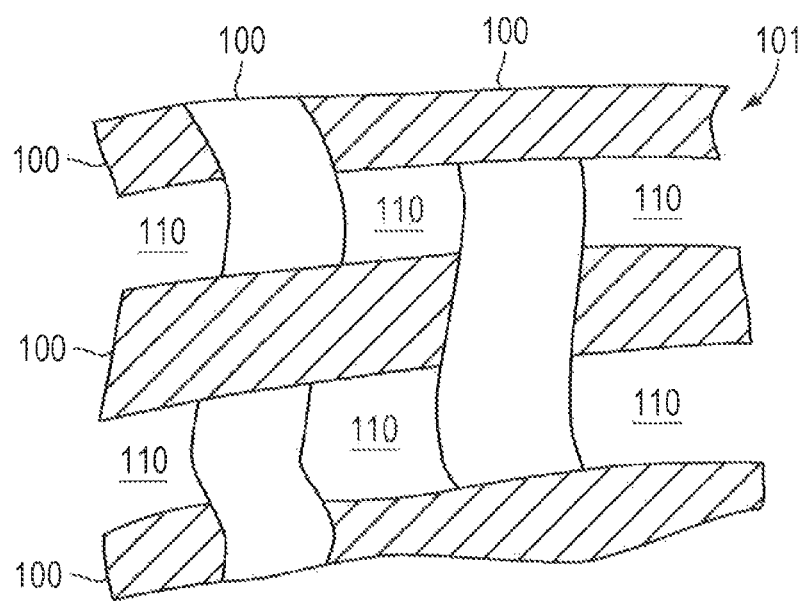

In yet another embodiment of making the invention, as shown in FIG. 7A, a first layer 101 in the tissue graft construct is made by weaving strips or strands 100a-e and 100g-k having a first density to form a mesh or lattice-like sheet. A second layer is also made by weaving strips or strands 100a-e and 100g-k having a second density to form a mesh or lattice-like sheet 101. The sheets 101 are then layered one on top of the other to form a tissue graft construct having layers of differing densities. The sheets may be compressed together. In yet another embodiment, as shown in FIG. 7B, a woven mesh or lattice-like sheet 101 is created but the weave is loose to create gaps 110 between the strips of ECM 100. Accordingly, in one embodiment a sheet of loose weave lattice 101 is sandwiched between two sheets, one of a first density, and the other of a second density, and the sheets are compressed together. The first sheet and the second sheet laminate or bond to one another through the gaps 110 in the lattice sheet 101.

In one embodiment according to the method of making the tissue graft composition, an adhesive such as fibrin glue, cyanoacrylate, thrombin/gelatin, PEG, or a solder such as albumin and laser energy, the application of heat at a temperature in the range of about 50° C. to 250° C. is additionally used between the layers to bond the layers of the tissue graft composition together. Cross-linking agents such as gluteraldehyde, dendrimers, and methylene blue, to name a few, can also be used to bond the layers of the tissue graft composition together. A peptide-linker could possibly also be used to bind the sheets. Another method of making the sheets is to expose them to heat while they are compressed or in close proximity. The heat generates bonds (crosslinks) between the collagen in each sheet.

In another aspect, the invention relates to the restoration or repair of tissue using the tissue composition according to the invention described above. A tissue graft composition comprising a first layer of ECM and a second layer of ECM, the first layer of ECM having a density in the range of about 400% to 125%, preferably, 300% to 150%, more preferably 200% to 175% of the density of the second layer is implanted at an anatomical site needing restoration or repair in a patient. In one embodiment of the method of the invention, one of the layers of the tissue graft composition has aponeurosis. In other embodiments, one or more layers may have UBM or other ECMs that include epithelial basement membrane, SIS, or UBS, for example. In a particular embodiment of the invention, the tissue graft composition that is implanted at an anatomical site comprises epithelial basement membrane on one surface of the tissue graft composition and on the other surface of the tissue graft composition, another ECM, aponeurosis, or a tissue repair site-specific ECM.

The tissue graft composition of the invention is not limited to the ECMs discussed above. For example, the tissue graft compositions may include one or more layers of ECM derived from treatment-site specific tissues. A treatment site specific tissue is a tissue harvested from the tissue at the site undergoing treatment, or harvested from the corresponding tissue as the site undergoing treatment from a donor mammal. For example, a few such treatment site-specific tissues include the ECM removed from skin, the ECM of the urinary bladder or the ECM of other epithelial organs and ECM of tendons, ligaments, cartilage, and skeletal or smooth muscle, for example. In this embodiment, one of the layers of ECM used in the tissue graft composition is an ECM corresponding to the ECM of the tissue undergoing restoration and derived from a donor mammal or from the patient undergoing the treatment.

Figure 8:
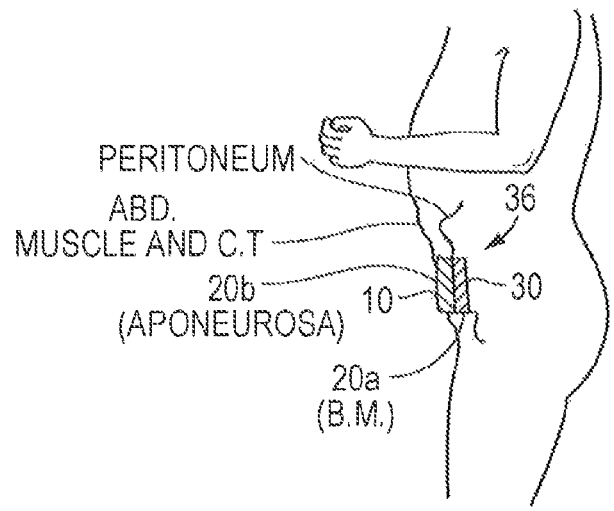
FIG. 8 illustrates an exemplary embodiment of the tissue graft composition implanted in the body wall according to one embodiment of the invention.

Referring to FIG. 8, in a particular embodiment of the method of treatment, a tissue graft composition 10 having epithelial basement membrane 30 on one surface and aponeurosis 20b on the other surface of the tissue graft composition is implanted at the site of an abdominal hernia 36. This embodiment of the tissue graft composition, has the advantage that the aponeurosis provides density, strength, elasticity and more prolonged bioresorption of the tissue graft composition than other ECMs, for example the epithelial basement membrane alone or ECMs such as UBM that include epithelial basement membrane. The epithelial basement membrane of the tissue graft composition initiates rapid restoration of the peritoneum on the peritoneal (inner) surface of the abdominal wall by attracting migration of host cells over and attachment to the epithelial basement membrane before the tissue graft composition is absorbed by the body.

The aponeurosis provides strength that is desirable for a graft implanted in the abdominal wall, an anatomical site subject to large forces and pressures. Aponeurosis also directs the natural restoration of the connective tissue of the abdominal wall because aponeurosis is a native tissue. Furthermore, because aponeurosis is more slowly bioresorbed than other ECMs including UBM, UBS and SIS, the aponeurosis provides strength over a sufficient length of time to ensure peritoneal epithelium as well as connective tissue restoration of the abdominal wall. In addition, because adhesions do not form at the implantation site when UBM is implanted, using UBM with the aponeurosis provides an additional advantage of UBM implants over traditional surgical repair procedures. The use of UBM provides native growth factors and bioactive components to the site of implantation which are released as UBM breaks down and is bioresorbed at the implantation site. UBM growth factors and bioactive components help speed up the healing process while the aponeurosis provides strength and support to the implantation site as it heals.

Figure 9:
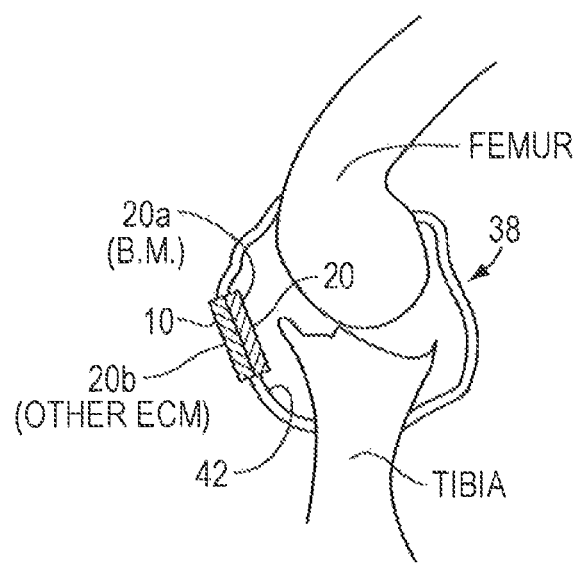
FIG. 9 illustrates an exemplary embodiment of the tissue graft composition implanted in the joint capsule according to one embodiment of the invention.

Referring to FIG. 9, in another embodiment, the method relates to restoration of a joint such as a knee joint by the implantation of the tissue graft composition 10 according to the invention. Exemplary synovial joints include temperomandibular, intervertebral, knee, hip, elbow, shoulder, wrist, or ankle joint, to name a few. The method provides a tissue graft composition comprising a first layer of ECM and a second layer of ECM, the first layer of ECM having a density in the range of about 400% to 1.25%, preferably 300% to 150%, more preferably 200% to 175% or the density of the second layer. The first layer of the tissue graft composition is bioresorbable within about 120 days and the second layer of the ECM is bioresorbable in about 30 days. In a particular embodiment, one surface of one layer 20a the tissue graft composition is epithelial basement membrane 30 and the other layer 20b is aponeurosis. The tissue graft composition 10 is implanted at the joint site 38 with the epithelial basement membrane surface 30 positioned on the luminal side of the synovial membrane 42 lining the joint.

As with the application of the tissue graft composition in the abdominal wall discussed above, the method of implanting the tissue graft composition of the invention to restore a joint has particular advantages over prior art compositions. This embodiment of the tissue graft composition when applied to a synovial joint has the advantage that the aponeurosis provides density, strength, elasticity, and more prolonged bioresorption than other ECMs. Prolonged bioresorption allows the tissue graft composition 10 to initiate rapid restoration by host cells of the epithelial tissue of the synovial joint, i.e., the synovial membrane 42, while the epithelial basement membrane 30 of the tissue graft composition 10 is still intact and before it is rapidly absorbed by the body. The tissue graft composition also allows restoration of the connective tissue components of the synovial joint, a restorative process that is significantly slower than epithelial repair, because the greater density, strength, and slower bioresorption of aponeurosis of the tissue graft composition maintains a stable environment at the implantation site for a sufficient length of time to allow connective tissue as well as epithelial tissue restoration to occur.

Figure 10A:
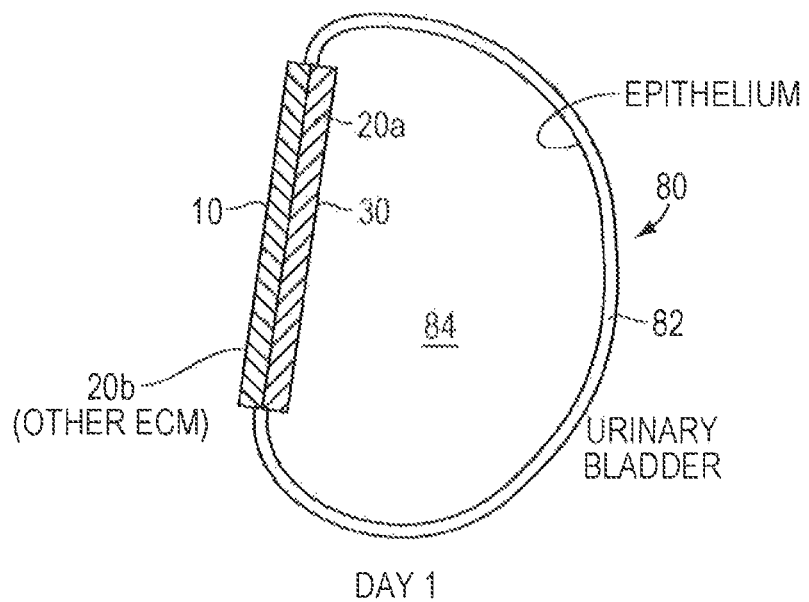
FIGS. 10A-C illustrate the appearance of an exemplary embodiment of the tissue graft composition implanted in the wall of the urinary bladder according to one embodiment of the invention at Day 1, Day 15 and 30 after implantation.
Figure 10B:
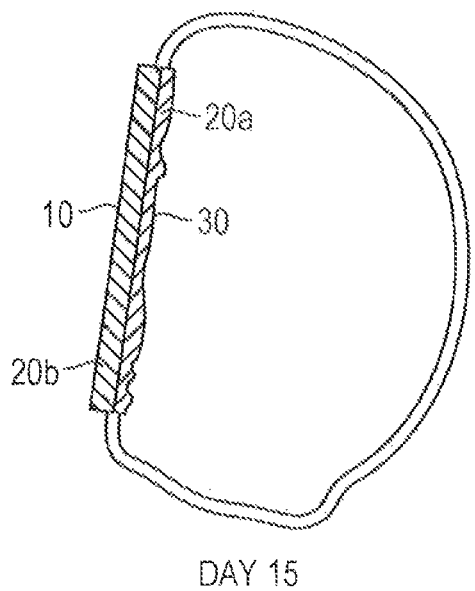
Figure 10C:
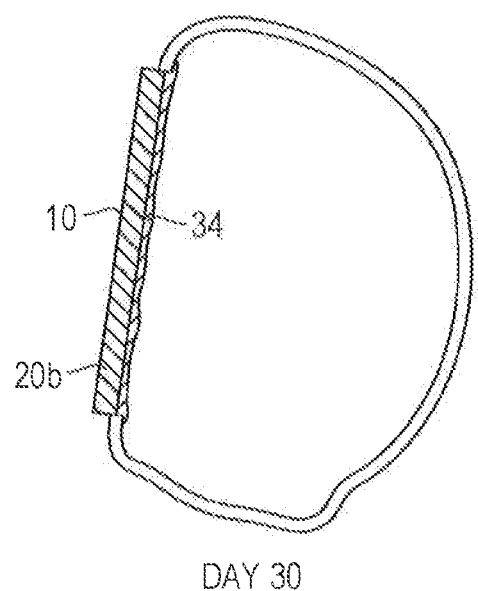

Referring to FIG. 10A-C, according to another embodiment, the method of the invention relates to restoration of the wall of the urinary bladder 80. The method provides a tissue graft composition having a first layer of ECM and a second layer of ECM, the first layer of ECM having a density in the range of about 400% to 125%, preferably 300% to 150%, more preferably 200% to 175% or the density of the second layer. The first layer of the tissue graft composition is bioresorbable within about 90 days and the second layer of the ECM is bioresorbable within about 30 days. In a particular embodiment, one surface of the first layer 20a of the tissue graft composition 10 is epithelial basement membrane 30. In a particular embodiment, the second layer of the tissue graft composition comprises aponeurosis or, alternatively, an ECM comprising a site-specific ECM such as devitalized smooth muscle layers of the urinary bladder of a mammal.

Referring to FIG. 10A, the exemplary tissue graft composition 10 is implanted in the wall 82 of the urinary bladder 80 at the site to be restored with the epithelial basement membrane 30 of the first layer 20a facing the lumen 84 of the portion of the wall 82 of the urinary bladder 80 undergoing treatment. Referring to FIG. 10B, at an exemplary 15 days after implantation, layer 20a is partially bioresorbed. Referring to FIG. 10C, host epithelium 32 is substantially restored at an exemplary 30 days post-implantation. Absorption of layer 20a may be faster or slower depending on various conditions and the time points illustrated are exemplary and not limiting. Layer 20b of the tissue graft composition remains even after 30 days thereby aiding in restoration of the bladder wall by ensuring that the appropriate conditions are in place for epithelial and connective tissue restoration at this tissue site which is subject to significant forces and pressures.

As in the case of the abdominal wall and the synovial joint discussed above, the method of implanting the tissue graft composition of the invention in the wall of the urinal bladder has particular advantages over prior art methods. This embodiment of the tissue graft composition when applied to the bladder wall has the advantage that the site-specific urinary bladder ECM provides density, strength, and more prolonged bioresorption than ECMs comprising the epithelial basement membrane. Furthermore, ECMs made from the external muscle layers of the bladder wall have the elasticity that is a requirement for normal bladder function. This allows the tissue graft composition patch to initiate rapid restoration of the epithelial tissue of the bladder wall, the urothelium, while the epithelial basement membrane of the tissue graft composition is still intact and before it is rapidly absorbed by the body.

The tissue graft composition also allows restoration of the connective tissue components of the bladder wall, a restorative process that, like joint tissue, is significantly slower than epithelial repair, because the greater density and strength and slower bioresorption of the site-specific urinary bladder of the tissue graft composition maintains a stable environment at the implantation site for a sufficient length of time to allow connective tissue restoration to occur.

Furthermore, the urinary bladder may be at least partially if not fully functional after implantation of the tissue graft composition because of the elasticity of the site-specific urinary bladder ECM in the second layer 20b.

What is claimed is:

1. A method for restoring a tissue at an anatomic site of a patient, comprising:
    providing a composition comprising
        an epithelial basement membrane and,
        an extracellular matrix material comprising a devitalized portion of a site-specific extracellular matrix material derived from an anatomic site of a mammalian source other than said patient wherein said site-specific extracellular matrix material corresponds to said anatomic site in need of restoration of said patient, and, one of said epithelial basement membrane and said extracellular matrix material has a plurality of raised elements and the other of said epithelial basement membrane and said extracellular matrix material has a plurality of depressions, wherein said raised elements are introduced into said depressions to join the epithelial basement membrane to said extracellular matrix material; and
    implanting said composition at the anatomic site of the patient.

2. The method of claim 1, wherein said epithelial basement membrane is located on a surface of said composition.

3. The method of claim 1 wherein said composition further comprises more than one layer of said site-specific extracellular matrix material.

4. The method of claim 1, wherein the composition is a tissue graft composition comprising said epithelial basement membrane on one surface of the tissue graft composition and said extracellular matrix material on another surface of said tissue graft composition.

5. The method of claim 1, wherein said extracellular matrix material comprises aponeurosis.

6. The method of claim 1, wherein said site-specific extracellular matrix material comprises an extracellular matrix of skin.

7. The method of claim 1, wherein said site-specific extracellular matrix material comprises an extracellular matrix material of intestine.

8. The method of claim 1, wherein said site-specific extracellular matrix material comprises an extracellular matrix material of urinary bladder.

9. The method of claim 1, wherein said site-specific extracellular matrix material comprises an extracellular matrix material of a tissue selected from the group consisting of smooth muscle and striated muscle.

10. The method of claim 1 further comprising an extracellular matrix material of tendon.

11. The method of claim 1 further comprising an extracellular matrix material of cartilage.

12. The method of claim 1 further comprising an extracellular matrix material of smooth muscle.

13. The method of claim 1 further comprising an extracellular matrix material of striated muscle.

14. The method of claim 1 further comprising an extracellular matrix material of aponeurosis.

15. The method of claim 1 wherein said depressions comprise valleys.

16. The method of claim 1 wherein said depressions comprise cups.

17. The method of claim 1 wherein said depressions comprise dimples.

18. The method of claim 1 wherein said depressions comprise cylinders.

\* \* \* \* \*

UNITED STATES PATENT AND TRADEMARK OFFICE
CERTIFICATE OF CORRECTION

| | | |
|---|---|---|
| PATENT NO. | : 8,541,032 B2 | Page 1 of 1 |
| APPLICATION NO. | : 13/649522 | |
| DATED | : September 24, 2013 | |
| INVENTOR(S) | : Bosley, Jr. et al. | |

It is certified that error appears in the above-identified patent and that said Letters Patent is hereby corrected as shown below:

On the Title page, item (54) and in the Specification, column 1, line 1, delete: "Tissue Graft Composition" and insert -- Variable Density Tissue Graft Composition and Methods of Making and Using the Same --

Signed and Sealed this
Eleventh Day of February, 2014

Michelle K. Lee
*Deputy Director of the United States Patent and Trademark Office*